(12) United States Patent
Draper

(10) Patent No.: US 11,000,648 B2
(45) Date of Patent: May 11, 2021

(54) RESETTABLE DRUG DELIVERY DEVICE

(71) Applicant: Sanofi, Paris (FR)

(72) Inventor: Paul Richard Draper, Evesham (GB)

(73) Assignee: Sanofi, Paris (FR)

( * ) Notice: Subject to any disclaimer, the term of this patent is extended or adjusted under 35 U.S.C. 154(b) by 1024 days.

(21) Appl. No.: 15/515,006

(22) PCT Filed: Oct. 9, 2015

(86) PCT No.: PCT/EP2015/073442
§ 371 (c)(1),
(2) Date: Mar. 28, 2017

(87) PCT Pub. No.: WO2016/055634
PCT Pub. Date: Apr. 14, 2016

(65) Prior Publication Data
US 2017/0239423 A1 Aug. 24, 2017

(30) Foreign Application Priority Data
Oct. 9, 2014 (EP) .................................... 14306598

(51) Int. Cl.
*A61M 5/315* (2006.01)
*A61M 5/20* (2006.01)
(Continued)

(52) U.S. Cl.
CPC .......... *A61M 5/31543* (2013.01); *A61M 5/20* (2013.01); *A61M 5/24* (2013.01);
(Continued)

(58) Field of Classification Search
CPC .. A61M 5/24; A61M 5/3126; A61M 5/31515; A61M 5/31541; A61M 5/31543;
(Continued)

(56) References Cited

U.S. PATENT DOCUMENTS 5,104,380 A * 4/1992 Holman ................. A61M 5/20
604/117
8,048,037 B2 11/2011 Kohlbrenner et al.
(Continued)

FOREIGN PATENT DOCUMENTS

| CN | 101563123 | 10/2009 |
| --- | --- | --- |
| CN | 103547303 | 1/2014 |

(Continued)

OTHER PUBLICATIONS

International Preliminary Report on Patentability in International Application No. PCT/EP2015/073442, dated Apr. 11, 2017, 8 pages.

(Continued)

*Primary Examiner* — William R Carpenter
*Assistant Examiner* — Larry R. Wilson
(74) *Attorney, Agent, or Firm* — Fish & Richardson P.C.

(57) ABSTRACT

The present disclosure is generally directed to a resettable drug delivery device for selecting and dispensing a number of user variable doses of a medicament. The drug delivery device comprises a housing, a cartridge holder, releasably attached to the distal end of the housing, a piston rod, engaging a housing insert and a drive member, a dose setting member, guided within the housing to allow rotation of the dose setting member during dose setting and dose dispensing, and a clutch for rotationally coupling the drive member (Continued)

and the dose setting member. The housing insert is rotationally constrained to the housing and is axially movable together with the drive member relative to the housing between a dose setting and dispensing position, and a resetting position. In the dose resetting position, the drive member is rotationally de-coupled from the housing.

15 Claims, 3 Drawing Sheets

(51) Int. Cl.
    *A61M 5/24*     (2006.01)
    *A61M 5/32*     (2006.01)
    *A61M 5/31*     (2006.01)

(52) U.S. Cl.
    CPC .... *A61M 5/31515* (2013.01); *A61M 5/31541* (2013.01); *A61M 5/31553* (2013.01); *A61M 5/31583* (2013.01); *A61M 5/31593* (2013.01); *A61M 5/3202* (2013.01); *A61M 2005/3126* (2013.01); *A61M 2205/581* (2013.01); *A61M 2205/582* (2013.01)

(58) Field of Classification Search
    CPC .......... A61M 5/31553; A61M 5/31578; A61M 5/3158; A61M 5/31581; A61M 5/31583; A61M 5/31585; A61M 5/31586; A61M 5/31593; A61M 2005/3125; A61M 2005/3126; A61M 2205/581; A61M 2205/582; A61M 5/3155; A61M 5/31551; A61M 5/31555

See application file for complete search history.

(56) References Cited

U.S. PATENT DOCUMENTS

| | | | | |
|---|---|---|---|---|
| 2010/0274198 A1* | 10/2010 | Bechtold | ................. | G06M 1/22 604/189 |
| 2012/0109075 A1* | 5/2012 | Harms | ................. | A61M 5/315 604/224 |
| 2012/0289909 A1* | 11/2012 | Raab | ................. | A61M 5/31585 604/211 |
| 2013/0204205 A1* | 8/2013 | Horlock | ............ | A61M 5/31555 604/211 |

FOREIGN PATENT DOCUMENTS

| | | |
|---|---|---|
| EP | 2 274 030 | 9/2012 |
| JP | 2012-500067 | 1/2012 |
| WO | WO 2009/105910 | 9/2009 |
| WO | WO 2009/132781 | 11/2009 |
| WO | WO 2010/020311 | 2/2010 |
| WO | WO 2011/154480 | 12/2011 |
| WO | WO 2012/130704 | 10/2012 |
| WO | WO 2014/033195 | 3/2014 |
| WO | WO-2014033195 A1 * | 3/2014 .......... A61M 5/3157 |

OTHER PUBLICATIONS

International Search Report and Written Opinion in International Application No. PCT/EP2015/073442, dated Jan. 12, 2016, 10 pages.

* cited by examiner

RESETTABLE DRUG DELIVERY DEVICE

CROSS-REFERENCE TO RELATED APPLICATIONS

This application is a U.S. national stage application under 35 USC § 371 of International Application No. PCT/EP2015/073442, filed on Oct. 9, 2015, which claims priority to European Patent Application No. 14306598.5 filed on Oct. 9, 2014, the entire contents of which are incorporated herein by reference.

TECHNICAL FIELD

The present disclosure is generally directed to a drug delivery device for selecting and dispensing a number of user variable doses of a medicament.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. Certain aspects are beneficial for reusable devices, which allow resetting of the device and a replacement of a cartridge. Resetting of the device typically involves moving a piston rod or lead screw from an extended (distal) position, i.e. a position after dose dispensing, into a more retracted (proximal) position.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

SUMMARY

Last dose mechanisms, which prevent setting a dose exceeding the amount of medicament remaining in the cartridge, comprise nuts driven by the rotation of the drive sleeve. However, they do all require that the relative timing of the axial position of the piston rod and the rotational position of the drive sleeve is maintained, i.e. they require that both the axial position of the piston rod and the rotational position of the drive sleeve (relative to the last dose nut) are reset together. An advantage of some embodiments may provide an improved resettable drug delivery device in which the last dose mechanism may be reset with fewer constraints, e.g. independent from the axial position of the piston rod.

In some aspects, the housing insert is rotationally constrained to the housing and is axially movable together with the drive member relative to the housing between a, preferably proximal, dose setting and dispensing position, and a, preferably distal, resetting position, in which the drive member is rotationally de-coupled from the housing. Allowing free rotation of the drive member relative to the housing during resetting of the devices not only permits resetting of the piston rod, which may wind back into the housing, but also permits resetting of a last dose mechanism which interacts with the drive member. It is a key feature that the drive member determines, by its axial position relative to the housing whether, the device is in a resetting mode or in a dose setting and dispensing mode. Preferably, the drive member is axially fixed in position during dose setting and dose dispensing. This may include holding the drive member in place by a spring biasing the drive member against an axial abutment.

Certain aspects can be useful in devices in which a relative rotation of the drive member is used for a last dose mechanism, because the housing insert and the drive member allow such a relative rotation of the drive member during dose setting and resetting while preventing undesired movement of the drive member during dose dispensing. The relative rotation of the drive member may be a relative rotation with respect to the housing. Preferably, it is a relative rotation with respect to the dose setting member. For example, a last dose nut may be provided interposed between the drive member and the dose setting member such that a relative rotation of the drive member and the dose setting member causes the last dose nut to travel axially until it reaches a last dose stop. In a preferred embodiment, the last dose nut is in threaded engagement with one of the drive member and the dose setting member, preferably the drive member, and rotationally constrained but axially movable relative to the other of the drive member and the dose setting member, preferably the dose setting member.

If the drug delivery device preferably comprises a last dose protection mechanism for preventing the setting of a dose, which exceeds the amount of liquid left in a cartridge, this has the advantage that the user knows how much will be delivered before starting the dose delivery. It also ensures that dose delivery stops in a controlled manner without the bung entering the neck portion of the cartridge where the diameter is smaller which may result in an underdose. For example, if the last dose protection mechanism comprises a nut member interposed between the drive member and any other component which rotates during dose setting and dose dispensing, the nut member only moves axially during dose setting and remains stationary with respect to this component during dose dispensing. The nut member may be a full nut or a part thereof, e.g. a half nut.

In a preferred embodiment the device further comprises at least one spring biasing the housing insert and the drive member into the resetting position. In other words, the housing insert and the drive member take up the resetting position under the action of the spring as soon as axial movement is allowed, e.g. by detaching the cartridge holder. The housing insert and the drive member may be coupled such that the housing insert entrains the drive member in an axial movement of the housing insert into the dose setting and dispensing position and that the drive member entrains the housing insert in an axial movement of the drive member into the resetting position. For example, this may be achieved by an axial abutment of the drive member and the housing insert. An embodiment may comprise a sleeve-like portion of the housing insert which is received in a tubular distal portion of the drive member to provide axial abutment but allow free rotation of the drive member relative to the housing insert.

It may be additionally advantageous to have an additional spring acting between the housing and housing insert, to provide further biasing of the housing insert in the distal direction (this decouples the force requirements of the clutch spring in its function for the dialing ratchet from the requirement to adequately bias the housing insert distally and react axial forces imparted by the user during resetting).

Resetting of the device may be started in different ways. As resetting typically involves replacing the cartridge, it is preferred to start resetting by detaching the cartridge holder from the housing to allow replacement of the cartridge. Preferably, the housing insert and the cartridge holder are coupled, for example by way of an axial abutment, such that the cartridge holder entrains the housing insert in an axial movement of the cartridge holder upon (re-)attachment of the cartridge holder to the housing. Removing the cartridge holder from the housing then allows axial displacement of the drive member and the housing insert, e.g. caused by the spring.

The piston rod may be in permanent threaded engagement with the housing insert. For example, the housing insert may comprise an inner thread engaging an outer thread of the piston rod, while the drive member is rotationally constrained to the piston rod.

In a further embodiment, the device comprises a locking element which is rotationally constrained to the housing and is axially movable relative to the housing between a, preferably proximal, dose setting position, in which the drive member is rotationally constrained to the housing, and a, preferably distal, dose dispensing position, in which the drive member is rotationally de-coupled from the housing. The locking element may be axially constrained to a dispense button or trigger located e.g. at the proximal end of the device. In other words, the axial position of the locking element defines whether the device is in the dose setting mode or in the dose dispensing mode. Preferably, the at least one spring biases the locking element into its dose setting position. As an alternative, an additional spring may be provided biasing the locking element into its dose setting position.

If the device has no dial extension, i.e. has a constant length irrespective of the size of the dose set, handling may be more user-friendly. In addition, this may make the device more reliable by preventing ingression of dirt or the like. For a device without dial extension, the dose setting member may be axially constrained to the housing.

According to a preferred embodiment, the drug delivery device is a spring driven device. A drive spring, preferably a torsion spring, may be interposed between the housing and the dose setting element. Providing a resilient drive member, such as a torsion spring, generating the force or torque required for dose dispensing reduces the user applied forces for dose dispensing. This is especially helpful for users with impaired dexterity. In addition, the dial extension of the known manually driven devices, which is a result of the required dispensing stroke, may be omitted by providing the resilient member because merely a small triggering stroke may be necessary for releasing the resilient member. The drive spring may be pre-charged, at least partly, and/or may be charged by a user during dose setting.

In a further development of this embodiment, the clutch between the dose setting member and the drive member is a slipping clutch with first clutch teeth on the drive member and second clutch teeth on a clutch member, e.g. a clutch plate or ring, which is rotationally constrained to the dose setting member during dose setting and dose dispensing. For example, the first and/or second clutch teeth may each be distributed as a ring of teeth, preferably facing in the axial direction. The clutch features and the corresponding clutch features may each comprise a series of teeth, preferably saw-teeth, which are allowed to slip over each other if not pressed against each other too firmly. In other words, the clutch features may be overhauled against the bias of the clutch spring by allowing the sleeve and/or the clutch element to translate axially against the force of the at least one spring (or alternatively a separate clutch spring). This may result in an oscillating axial movement of the sleeve and/or the clutch element due to continued disengagement and following re-engagement into the next detented position. An audible click may be generated by this re-engagement, and tactile feedback may be given by the change in torque input required.

Preferably, the clutch between the drive member and the dose setting member is a slipping clutch which allows relative rotation between the drive member and the dose setting member in both directions during dose setting for increasing or decreasing a set dose. If the device is a spring driven device, the clutch teeth may be designed to provide a different resistance for overcoming the clutch depending on the direction of the relative rotation. For example, the ramp angle may be shallower resulting in a lower resistance in the dose increasing direction and steeper resulting in a higher resistance in the dose decreasing direction.

In another preferred embodiment, the drug delivery device further comprises a gauge element radially interposed between the outer housing and the dose setting element. The gauge element is axially movable relative to the outer housing and in threaded engagement with the dose setting element. The outer housing may comprise at least one aperture and the gauge element may comprise at least one aperture. If the dose setting element is a number sleeve which comprises markings on its outer surface, at least one of the markings is visible through the aperture in the gauge element and the aperture in the outer housing during dose setting and dose dispensing. The term aperture may include a simple opening the outer housing or gauge element or a transparent window or lens. A window in the outer housing may be incorporated using a 'twin-shot' molding technology. For example, the outer housing is molded during a 'first shot' in a translucent material, and the outer cover of the outer housing is molded during a 'second shot' in an opaque material.

The gauge element may be axially guided within the outer housing such that rotation of the dose setting element causes an axial displacement of the gauge element. The position of the gauge element may thus be used to identify the actually set and/or dispensed dose. Different colors of sections of the gauge member may facilitate identifying the set and/or dispensed dose without reading numbers, symbols or the like on a display. As the gauge element is in threaded engagement with the dose setting element, rotation of the dose setting element causes an axial displacement of the gauge element relative to the dose setting element and relative to the outer housing. The gauge element may have the form of a shield or strip extending in the longitudinal direction of the device. As an alternative, the gauge element may be a sleeve. In an embodiment, the dose setting element is marked with a sequence of numbers or symbols arranged on a helical path. With the dose setting element located radially inwards of the gauge element, this allows that at least one of the numbers or symbols on the dose setting element is visible through the aperture or window. In other words, the gauge element may be used to shield or cover a portion of the dose setting element and to allow view only on a limited portion of the dose setting element. This function may be in addition to the gauge element itself being suitable for identifying or indicating the actually set and/or dispensed dose.

In general, the concept of the gauge element and the dose setting element is applicable for various types of devices with or without a drive spring. In a preferred embodiment, the dose setting element, during dose setting, is adapted to undergo a mere rotational movement within the outer housing and relative to the outer housing. In other words, the dose setting element does not perform a translational movement during dose setting. This prevents that the dose setting element is wound out of the outer housing or that the outer housing has to be prolonged for covering the dose setting element within the outer housing.

The relative movements of the gauge element and the dose setting element may further be used to define the minimum dose position and the maximum dose position. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring torque needed for dispensing very high doses, while still being suitable for a wide range of patients needing different dose sizes. Preferably, the limits for the minimum dose and the maximum dose are provided by hard stop features. For example, the gauge element comprises a minimum dose rotational stop and a maximum dose rotational stop and the dose setting element comprises a minimum dose rotational counter stop and a maximum dose rotational counter stop. Abutment of the respective stop and counter stop blocks further relative movement between the gauge element and the dose setting element. As the dose indicator rotates relative to the gauge element during dose setting and during dose dispensing, these two components are suitable to form a reliable and robust limiter mechanism.

The injection device may comprise at least one clicker mechanism for generating a tactile and/or audible feedback. A feedback may be generated during dose setting (increasing and/or decreasing a dose), dose dispensing and/or at the end of dose dispensing.

According to a preferred embodiment, a dose is set by rotating a dial grip located at the proximal end of the housing. Delivery of a dose is initiated by pressing the button and displacing the button axially in the distal direction. Dose delivery continues while the button remains depressed, until the complete set dose has been delivered. The mechanism provides audible, visual and tactile feedback both on the setting and delivery of each dose. Preferably, the mechanism contains a helical drive spring to store energy, which is charged during setting of the dose by the action of the user rotating the dial grip. The spring energy is stored until the mechanism is triggered for dispense at which point the energy stored is used to deliver the medicament from the cartridge to the user. Preferably, any dose size can be selected between zero and a pre-defined maximum, in increments to suit the medicament and user profile. The mechanism permits cancelling of a dose without any medicament being dispensed by rotation of the dial grip in the opposing direction to when selecting a dose.

In a further embodiment, the spline teeth on either the drive sleeve or the locking element are angled so that when the button is released the re-engagement of the spline teeth fractionally backwinds the drive sleeve. This removes the engagement of the number sleeve to the gauge element at the zero dose stop abutment, which compensates for the effect of clearances in the mechanism (for example due to tolerances) which could otherwise lead to slight advancement of the piston rod and medicament dispense when the device is dialed for the subsequent dose (due to the number sleeve zero dose stop no longer restraining the mechanism and instead the restraint returning to the splines between the drive sleeve and housing).

A further independent aspect refers to a method of resetting a drug delivery device, e.g. a device as described above, comprising the steps of unscrewing the cartridge holder, pushing back the piston rod either by a new cartridge or manually, and re-attaching the cartridge holder together with a new cartridge. Preferably, unscrewing the cartridge holder allows the trigger spring to move the housing insert, drive sleeve and clutch plate axially in a distal direction. This axial travel is preferably sufficient to disconnect the splines between the locking element and the drive sleeve and the splines between the clutch plate and the number sleeve. It may also remove some compression from the trigger spring. In the second step of this method, the user may fit a new cartridge into the cartridge holder, and the bearing and piston rod are pushed back into the mechanism. As the piston rod is returned into the mechanism, a rotation in the piston rod may be generated due to the thread interface with housing insert. This piston rod rotation causes the drive sleeve to rotate due to their spline interface, which acts to backwind the last dose nut towards its start position. Finally, towards the end of reset, the cartridge holder preferably contacts the housing insert and at this point the bearing, piston rod and last dose nut may have reached a fully reset position.

Rotation of the cartridge holder preferably acts to move the housing insert and drive sleeve in a proximal direction, reengaging splines between the drive sleeve and locking element, and splines between clutch plate and number sleeve.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra-low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ, and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Non-limiting, exemplary embodiments will now be described with reference to the accompanying drawings, in which:

FIG. 2 shows an exploded view of the components of the device of FIG. 1a;

FIGS. 7a-c show in sectional views the sequence of resetting the device of FIG. 1a.

DETAILED DESCRIPTION OF THE DRAWINGS

Figure 1A:
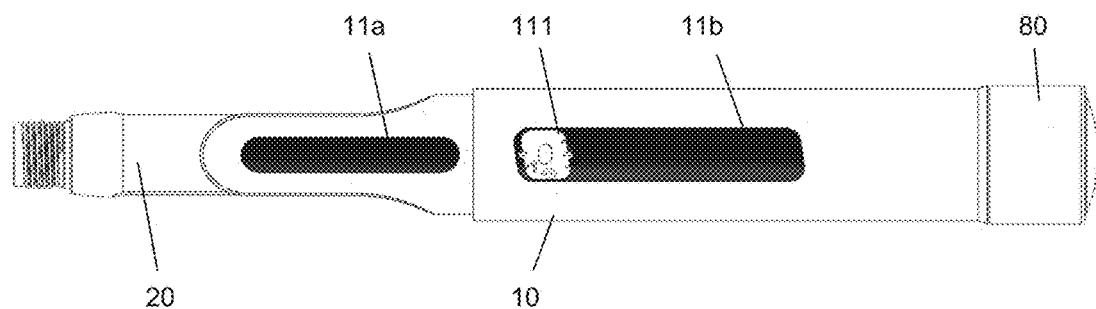
FIG. 1a shows a top view of the drug delivery device in the minimum dose position.
Figure 2:
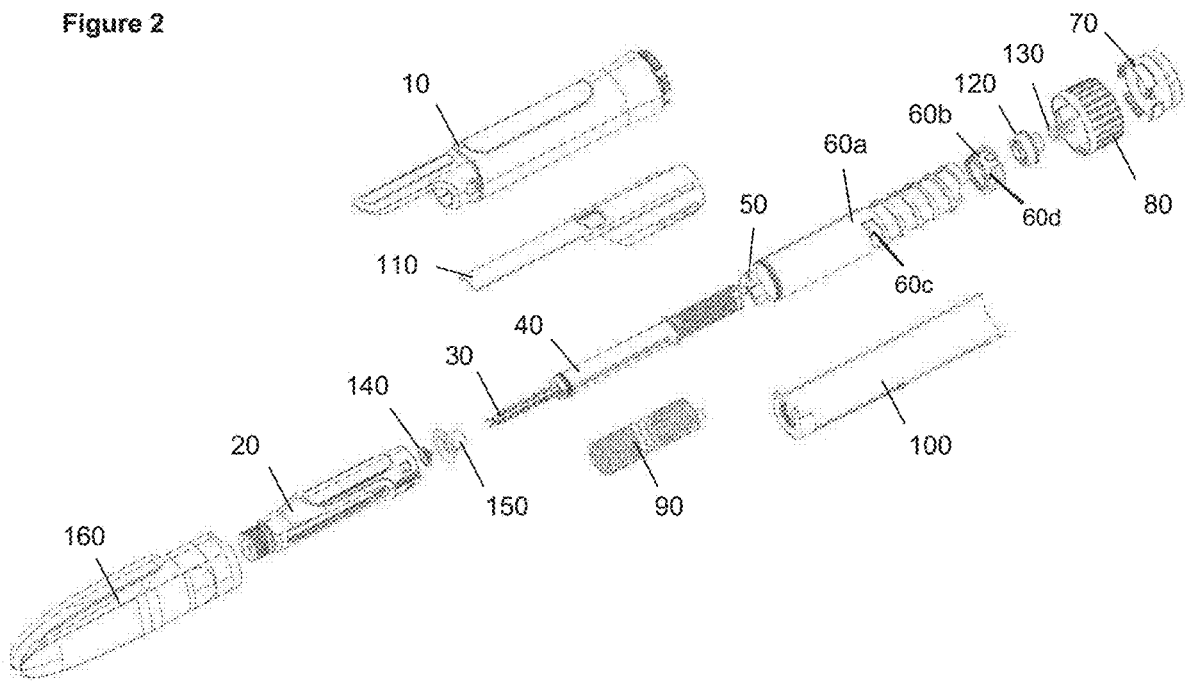
Figure 3:
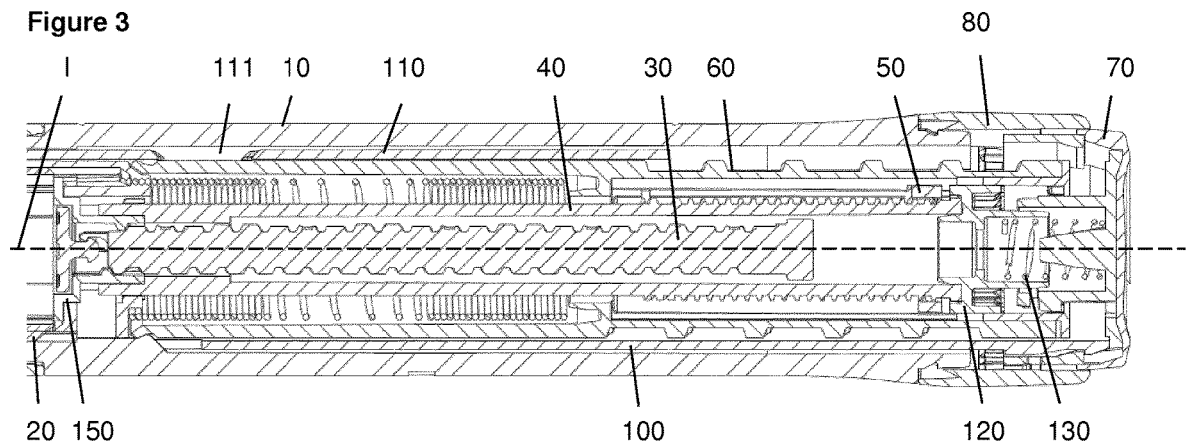
FIG. 3 shows a sectional view of the device of FIG. 1a in the dose setting mode.
Figure 4A:
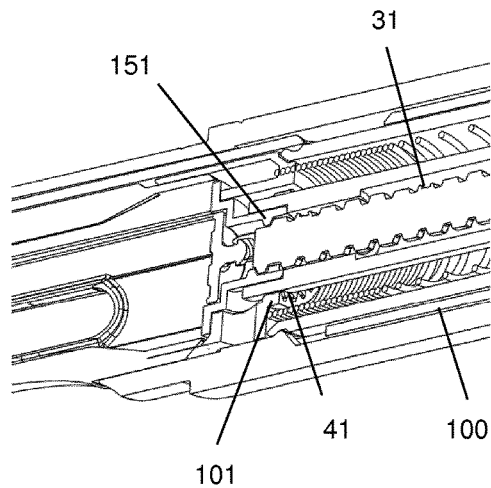
FIGS. 4a, b show in sectional views details of the device of FIG. 1a in the dose setting mode.
Figure 4B:
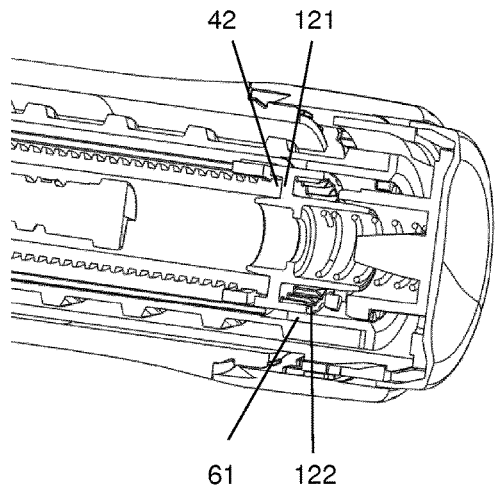

FIG. 1a shows a drug delivery device in the form of an injection pen. The device has a distal end (left end in FIG. 1a) and a proximal end (right end in FIG. 1a). The component parts of the drug delivery device are shown in FIG. 2. The drug delivery device comprises a body or housing 10, a cartridge holder 20, a lead screw (piston rod) 30, a drive sleeve 40, a nut 50, a dose setting member which is a dose indicator (number sleeve) 60, a button 70, a dial grip or dose selector 80, a torsion spring 90, a locking element 100, a gauge element 110, a clutch element 120, a clutch spring 130, a bearing 140, a housing insert 150 and a cap 160. A needle arrangement (not shown) with a needle hub and a needle cover may be provided as additional components, which can be exchanged as explained above. All components are located concentrically about a common principal axis I of the mechanism which is shown in FIG. 3.

The housing 10 or body is a generally tubular element. The housing 10 provides location for a liquid medication cartridge and cartridge holder 20, windows 11a, 11b for viewing the dose number on the dose indicator 60 and the gauge element 110, and a feature on its external surface, e.g. a circumferential groove, to axially retain the dose selector 80. The housing 10 further has at least one internal, axially orientated slot or the like for axially guiding the gauge element 110. Further, housing insert 150 is axially guided within housing 10 such that relative rotation is prevented, while, preferably limited, axial relative movement is allowed. In addition, locking element 100 is axially guided in housing 10 such that relative rotation is prevented while axial relative movement is allowed.

The cartridge holder 20 contains the replaceable cartridge and acts to limit the axial travel of the housing insert 150 in the distal direction. When the cartridge holder 20 is removed, the trigger spring 130 forces the housing insert 150, drive sleeve 40 and clutch plate 120 axially in a distal direction, disengaging the spline teeth 41, 101 between the locking element 100 and the drive sleeve 40 and the spline teeth between the clutch plate 120 and the number sleeve 60, allowing the device to be reset. A bias spring (not shown) may be provided to act between the housing 10 and the cartridge to bias the cartridge in a distal direction. The removable cap 160 is provided to fit over the cartridge holder 20 and may be retained via clip features on the housing 10.

The piston rod 30 is an elongate lead screw element with an outer thread 31 and at least one axially extending spline or rib. The piston rod 30 is rotationally constrained to the drive sleeve 40 via this splined interface. When rotated, the piston rod 30 is forced to move axially relative to the housing 10, through its threaded interface 31, 151 with the housing insert 150. The bearing 140 is attached to the distal end the piston rod 30, e.g. by a snap connection.

The drive sleeve 40 is a tubular member surrounding the piston rod 30 and being at least in parts received within the dose setting member 60. The drive sleeve 40 extends from the interface 42, 121 with the number sleeve 60 (via the clutch plate 120) down to a splined tooth interface 41, 101 with the locking element 100. This provides a rotational constraint to the drive sleeve 40 during dose setting. When the button 70 is pressed, the locking element 100 is moved axially in a distal direction such that these spline teeth 41, 101 are disengaged, allowing the drive sleeve 40 to rotate under the action of the drive spring 90, dispensing the set dose.

The last dose nut 50 is located between the number sleeve 60 and the drive sleeve 40. It is rotationally constrained to the number sleeve 60, via a splined interface. It moves along a helical path relative to the drive sleeve 40, via a threaded interface, when relative rotation occurs between the number sleeve 60 and drive sleeve 40, i.e. during dialing and resetting only.

The dose setting member 60 is a tubular number sleeve which is constrained, via a clip at its distal end, to the housing 10 to allow rotation but not axial translation in all conditions. The number sleeve 60 is marked with a sequence of numbers, which are visible through opening 111 in the gauge element 110 and the slot-like window 11b in the housing 10, to denote the dialed dose of medicament. In the embodiment shown in the Figures, the dose setting member 60 comprises a lower part 60 a and an upper part 60 b which are fixed to each other during assembly. The lower part 60 a is provided with the numbers and with the thread engaging the gauge element 110. The upper part 60 b comprises a splined interface 61, 122 with the clutch plate 120. The gauge element comprises a minimum dose rotational stop and a maximum dose rotational stop and the dose setting element comprises a minimum dose rotational counter stop 60c and a maximum dose rotational counter stop 60d.

The button 70 is splined to the upper part 60b of number sleeve 60 when in the dialing condition. This spline interface is disconnected when the button 70 is pressed to trigger a dispense. When depressed, the button 70 is rotationally constrained to the housing 10 via a splined engagement. The dose selector 80 is radially constrained to the housing 10 and rotationally constrained to the button 70. Further, the button 70 comprises a compliant clicker arm interacting with ratchet features on the upper part 60b during dose dispensing.

The dial grip 80 is radially constrained to the housing 10 and rotationally constrained to the button 70.

The drive spring 90 is attached at one end to the locking element 100 and at the other end to the number sleeve 60. The drive spring 90 is pre-wound upon assembly, such that it applies a torque to the number sleeve 60 when the mechanism is at zero units dialed. The action of rotating the dose selector 80, to set a dose, rotates the number sleeve 60 relative to the housing 10, and charges the drive spring 90.

The locking element 100 mainly has the form of an arm or a half-shell and is rotationally splined to the housing 10 and axially constrained to the button 70 in all conditions. It is axially movable relative to the housing 10 between a proximal dose setting position (locking the drive sleeve 40 to the housing) and a distal dose dispensing position (allowing rotation of the drive sleeve 40). The locking element 100 has teeth 101 engaging corresponding teeth 41 of the drive sleeve when in its dose setting position.

The gauge element 110 is constrained to prevent rotation but allow translation relative to the housing 10 via a splined interface. The gauge element 110 has helical features on its inner surface which engage with the helical thread cut in the dose setting member 60 such that rotation of the dose setting member 60 causes axial translation of the gauge element 110. These helical features on the gauge element 110 also create stop abutments against the end of the helical cut in the dose setting member 60 to limit the minimum and maximum dose that can be set. An opening or window 111 allows viewing a portion of the dose setting member 60 through the gauge element 110.

The clutch plate 120 is splined to the upper part 60*b* of number sleeve 60 via interface 61, 122 when in the dialing and dispensing conditions. On entry to the reset condition the clutch plate 120 moves axially in a distal direction, disconnecting this spline interface 61, 122 with the upper part 60*b* of number sleeve 60. The clutch plate 120 is also coupled to the drive sleeve 40 via a ratchet interface 42, 121, which occurs on an axial abutment. The ratchet provides a detented position between the number sleeve 60 and drive sleeve 40 corresponding to each dose increment, and engages different ramped tooth angles during clockwise and anti-clockwise relative rotation.

The clutch or trigger spring 130 is axially interposed between the clutch 120 and the button 70. In the at rest position, the trigger spring 130 applies a biasing force on the button 70 in the proximal direction to ensure that the button 70 splines are engaged with the upper part 60*b* of number sleeve 60.

The bearing 140 is axially constrained to the piston rod 30 and acts on the bung within the liquid medicament cartridge.

The housing insert 150 is rotationally splined to the housing 10 and biased in a distal direction against the cartridge holder 20 by the trigger spring 130. The axial positions of the drive sleeve 40 and clutch plate 120 are also defined by the action of the trigger spring 130, which applies a biasing force in the distal direction to ensure the drive sleeve 40 splines are engaged with the locking element 100 and the ratchet 42, 121 between the drive sleeve 40 and clutch plate 120 is engaged. The maximum travel in the distal direction of these components is defined by a stop face between the housing insert 150 and the cartridge holder 20.

With the device in the at rest condition or dose setting mode as shown in FIGS. 1*a*, 3, 4*a* and 4*b*, the number sleeve 60 is positioned against its zero dose abutment with the gauge element 110, and the button 70 is not depressed. Dose marking '0' on the number sleeve 60 is visible through the windows 11*b* and 111 of the housing 10 and gauge element 110. The drive spring 90, which has a number of pre-wound turns applied to it during assembly of the device, applies a torque to the number sleeve 60 and is prevented from rotating by the zero dose abutment. It is also possible to back-wind the mechanism slightly due to an offset between the zero dose stop and the angular offset of the drive sleeve 40 spline teeth. This has the effect of preventing possible weepage when a dose is dialed and the zero dose abutment is disengaged.

The user selects a variable dose of liquid medicament by rotating the dose selector 80 clockwise, which generates an identical rotation in the number sleeve 60. Rotation of the number sleeve 60 causes charging of the drive spring 90, increasing the energy stored within it. As the number sleeve 60 rotates, the gauge element 110 translates axially due to its threaded engagement thereby showing the value of the dialed dose. The gauge element 110 has flanges either side of the window area which cover the numbers printed on the number sleeve 60 adjacent to the dialed dose to ensure only the set dose number is made visible to the user.

Figure 1B:
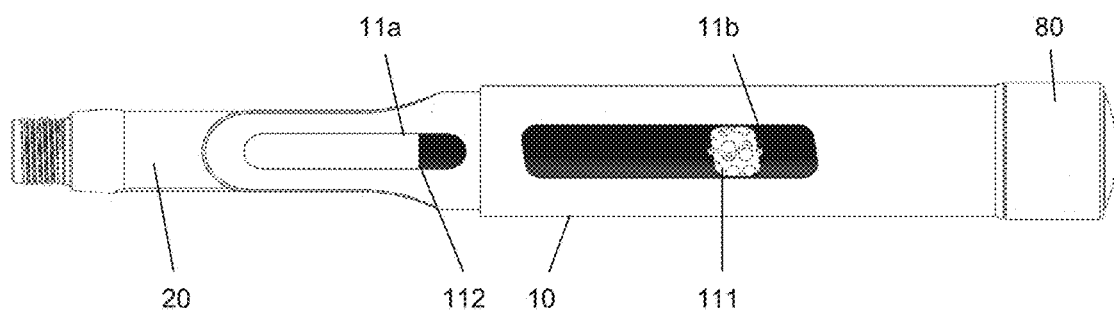
FIG. 1b shows a top view of the drug delivery device of FIG. 1a with a dose of 96 units dialed.

One specific element of this type of mechanism is inclusion of a visual feedback feature in addition to the discrete dose number display typical on devices of this type. The distal end 112 of the gauge element 110 creates a sliding scale (although this could be formed using a separate component engaged with the number sleeve 60 on a different helical track if desired) through the small window 11*a* in the housing 10. As a dose is set by the user the gauge element 110 translates axially, the distance moved proportional to the magnitude of the dose set. This feature gives clear feedback to the user regarding the approximate size of the dose set. Comparing FIGS. 1*a* and 1*b* shows how the distal end 112 of the gauge element 110 moves proximally during dose setting. The dispense speed of an auto-injector mechanism may be higher than for a manual injector device, so it may not be possible to read the numerical dose display during dispense. The gauge element 110 feature provides feedback to the user during dispense regarding dispense progress without the need to read the dose number itself.

The gauge element 110 display may be formed by an opaque sliding element revealing a contrasting colored component underneath. Alternatively, the concealed component may be printed with coarse dose numbers or other indices to provide more precise resolution. In addition, the gauge element 110 display simulates a syringe action during dose set and dispense.

The drive sleeve 40 is prevented from rotating as the dose is set due to the engagement of its splined teeth 41 with teeth 101 of the locking element 100, and the clutch plate 120 is rotated due to the engagement of its splined teeth 61, 122 with the number sleeve 60. Relative rotation must therefore occur between the clutch plate 120 and drive sleeve 40 via the ratchet interface 42, 121.

The user torque required to rotate the dose selector 80 is a sum of the torque required to wind up the drive spring 90, and the torque required to overhaul the ratchet feature 42, 121. The trigger spring 130 is designed to provide an axial force to the ratchet feature and to bias the clutch plate 120 onto the drive sleeve 40. This axial load acts to maintain the ratchet teeth engagement of the clutch plate 120 and drive sleeve 40. The torque required to overhaul the ratchet 42, 121 in the dose set direction is a function of the axial load applied by the trigger spring 130, the clockwise ramp angle of the ratchet 42, 121, the friction coefficient between the mating surfaces and the mean radius of the ratchet features 42, 121.

As the user rotates the dose selector 80 sufficiently to increment the mechanism by 1 increment, the clutch plate 120 rotates relative to the drive sleeve 40 by 1 ratchet tooth. At this point the ratchet teeth 42, 121 re-engage into the next detented position. An audible click is generated by the ratchet re-engagement, and tactile feedback is given by the change in torque input required. Relative rotation of the number sleeve 60 and the drive sleeve 40 causes the last dose nut 50 to travel along its threaded path, towards its last dose abutment on the drive sleeve 40.

With no user torque applied to the dose selector 80, the number sleeve 60 is now prevented from rotating back due to the torque applied by the drive spring 90, solely by the ratchet engagement 42, 121 between the clutch plate 120 and the drive sleeve 40. The torque necessary to overhaul the ratchet in the anti-clockwise direction is a function of the axial load applied by the trigger spring 130, the anti-clockwise ramp angle of the ratchet 42, 121, the friction coefficient between the mating surfaces and the mean radius of the ratchet features. The torque necessary to overhaul the ratchet must be greater than the torque applied to the number sleeve 60 (and hence clutch plate 120) by the drive spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interfaces 42, 121 between the clutch plate 120 and drive sleeve 40 is repeated for each dose increment. Additional energy is stored within the drive spring 90 for each dose increment and audible and tactile feedback is provided for each increment dialed by the re-engagement of the ratchet teeth 42, 121. The torque required to rotate the dose selector 80 increases as the torque required to wind up the drive spring 90 increases. The torque required to overhaul the ratchet 42, 121 in the anti-clockwise direction must therefore be greater than the torque applied to the number sleeve 60 by the drive spring 90 when the maximum dose has been reached.

If the user continues to increase the selected dose until the maximum dose limit is reached, the number sleeve 60 engages with its maximum dose abutment on the gauge element 110. This prevents further rotation of the number sleeve 60, clutch plate 120 and dose selector 80.

Figure 7A:
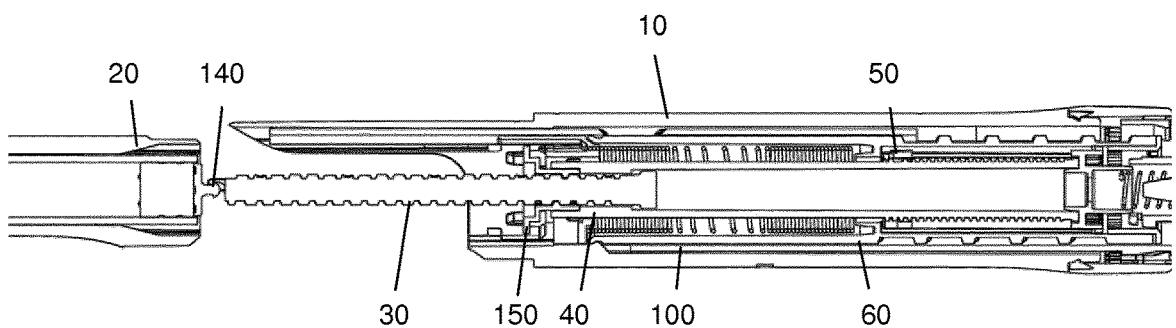
Figure 7B:
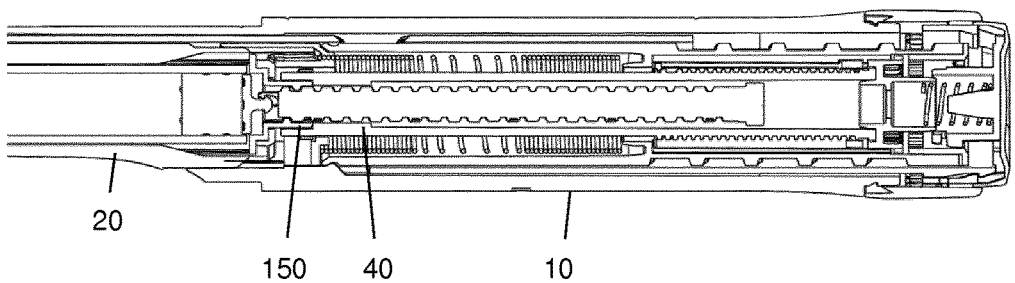
Figure 7C:
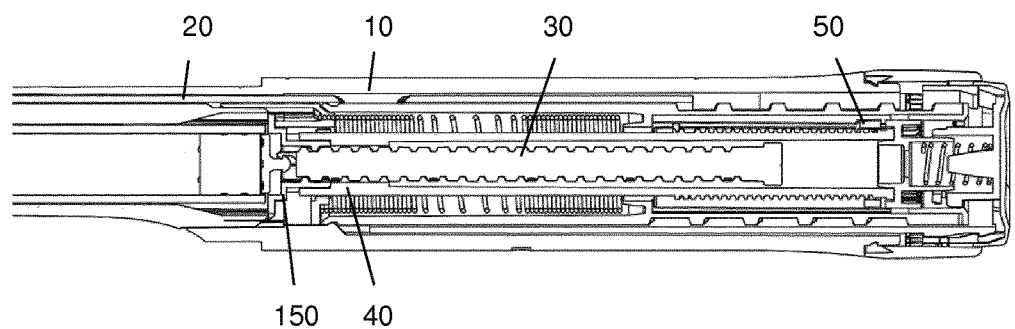

Depending on how many increments have already been delivered by the mechanism, during selection of a dose, the last dose nut 50 may contact its last dose abutment with the drive sleeve 40 as shown in FIG. 7a. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the drive spring 90, to overhaul the ratchet 42, 121 between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the drive spring 90. The relative rotation between the number sleeve 60 and drive sleeve 40 causes the last dose nut 50 to return along its helical path, away from the last dose abutment.

Figure 5A:
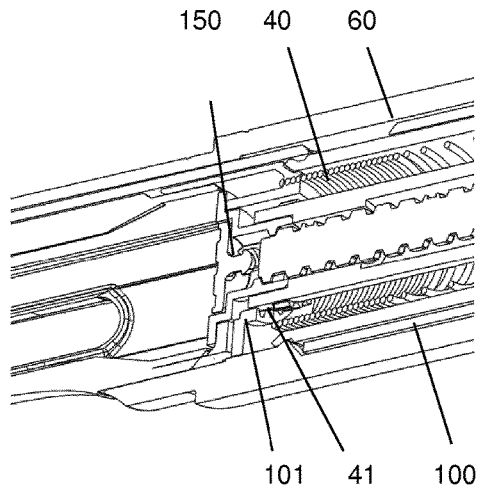
FIGS. 5a, b show in sectional views details of the device of FIG. 1a in the dose dispensing mode.
Figure 5B:
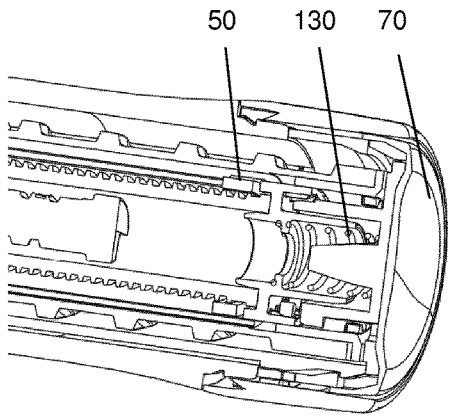
Figure 6A:
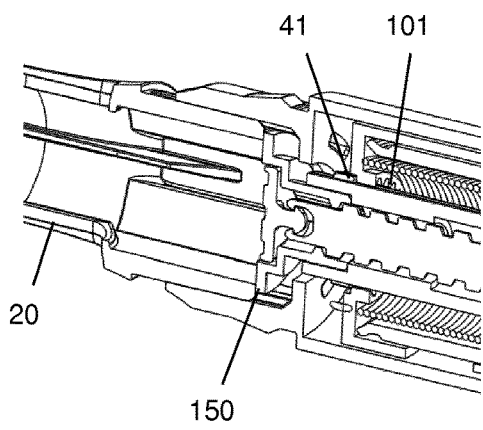
FIGS. 6a, b show in sectional views details of the device of FIG. 1a in the resetting mode.
Figure 6B:
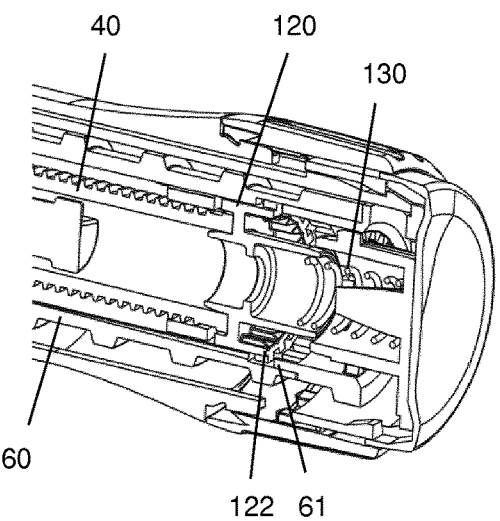

With the mechanism in a state in which a dose has been selected, the user is able to activate the mechanism to commence delivery of a dose. Delivery of a dose is initiated by the user depressing the button 70 axially as shown in FIGS. 5a and 5b.

When the button 70 is depressed, splines between the button 70 and number sleeve 60 are disengaged, rotationally disconnecting the button 70 and dose selector 80 from the delivery mechanism. Splines on the button 70 also engage with splines on the housing 10 (such that the dose selector 80 and button 70 do not rotate during dispense). The button 70 force acts on the locking element 100 which travels axially and disconnects the splined engagement 41, 101 with the drive sleeve 40, allowing rotation of the drive sleeve 40. The force on the ratchet 42, 121 between clutch plate 120 and drive sleeve 40 is increased by compression of the trigger spring 130, causing these components to spin together rather than overhaul the ratchet 42, 121, driven by the drive spring 90 via the number sleeve 60. Rotation of the drive sleeve 40 causes the piston rod 30 to rotate due to their splined engagement, and the piston rod 30 then advances due to its threaded engagement 31, 151 to the housing insert 150. The number sleeve 60 rotation also causes the gauge element 110 to traverse axially back to its zero position whereby the zero dose abutment stops the mechanism.

Tactile feedback during dose dispense is provided via a compliant cantilever clicker arm integrated into the button 70. This interfaces radially with ratchet features on the clutch plate 120. During dispense, as the clutch plate 120 rotates and the button 70 is rotationally coupled to the housing 10, the ratchet features engage with the clicker arm to produce an audible click with each dose increment delivered.

Delivery of a dose continues via the mechanical interactions described above while the user continues to depress the button 70. If the user releases the button 70, the trigger spring 130 returns the button 70 to its at rest position, the drive sleeve 40 becomes rotationally constrained and delivery of a dose is halted.

During delivery of a dose, the drive sleeve 40 and number sleeve 60 rotate together, so that no relative motion in the last dose nut 50 occurs. The last dose nut 50 therefore travels axially on the drive sleeve 40 during dialing (and reset) only.

Once the delivery of a dose is stopped by the number sleeve 60 returning to the zero dose abutment with the gauge element 110, the user may release the button 70, which will re-engage spline teeth 41 of the drive sleeve 40 with teeth 101 of the locking element 100. The mechanism is now returned to the at rest condition.

The mechanism may incorporate a bias spring (not shown in the embodiment) which acts on the rear face of the cartridge. This aids dose accuracy as it ensures the cartridge is always biased distally, removing the effect of the tolerance on the cartridge length and the possibility of the cartridge moving proximally when a needle is fitted to the device.

It is possible to angle the spline teeth 41, 101 on either the drive sleeve 40 or locking element 100 so that when the button 70 is released the re-engagement of the spline teeth 41, 101 fractionally backwinds the drive sleeve 40 thereby removing the engagement of the number sleeve 60 to the gauge element 110 zero dose stop abutment. This compensates for the effect of clearances in the mechanism (for example due to tolerances) which could otherwise lead to slight advancement of the piston rod 30 and medicament dispense when the device is dialed for the subsequent dose (due to the number sleeve 60 zero dose stop no longer restraining the mechanism and instead the restraint returning to the splines between the drive sleeve 40 and housing 10).

To reset the mechanism, the user first unscrews the cartridge holder 20, which allows the trigger spring 130 to move the housing insert 150, drive sleeve 40 and clutch plate 120 axially in a distal direction. This axial travel is sufficient to disconnect the splines 41, 101 between the locking element 100 and the drive sleeve 40 and the splines 61, 122 between the clutch plate 120 and the number sleeve 60. It also removes some compression from the trigger spring 130.

The user can then fit a new cartridge into the cartridge holder 20, and the bearing 140 and piston rod 30 can be pushed back into the mechanism. As the piston rod 30 is returned into the mechanism, a rotation in the piston rod 30 is generated due to the thread interface 31, 151 with housing insert 150. This piston rod 30 rotation causes the drive sleeve 40 to rotate due to their spline interface, which acts to backwind the last dose nut 50 towards its start position.

Towards the end of reset, the cartridge holder 20 contacts the housing insert 150 and at this point the bearing 140, piston rod 30 and last dose nut 50 have reached a fully reset position. Rotation of the cartridge holder 20 acts to move the housing insert 150 and drive sleeve 40 in a proximal direction, reengaging splines 41, 101 between the drive sleeve 40 and locking element 100, and splines 61, 122 between clutch plate 120 and number sleeve 60.

| Reference Numerals: | |
|---|---|
| 10 | outer housing |
| 11a | opening (window) |
| 11b | opening (window) |
| 20 | cartridge holder |
| 30 | piston rod (lead screw) |
| 31 | outer thread |
| 40 | drive sleeve |
| 41 | teeth |
| 42 | ratchet teeth |
| 50 | nut |
| 60 | dose setting element |
| 61 | spline |
| 70 | button |
| 80 | dose selector |
| 90 | torsion spring |
| 100 | locking element |
| 101 | teeth |
| 110 | gauge element |
| 111 | opening |
| 112 | distal end |
| 120 | clutch |
| 121 | ratchet teeth |
| 122 | spline |
| 130 | trigger spring |
| 140 | bearing |
| 150 | housing insert |
| 151 | thread |
| 160 | cap |
| I | longitudinal axis |

The invention claimed is:

1. A drug delivery device for selecting and dispensing a number of user variable doses of a medicament, the drug delivery device comprising
   a housing having a distal end and a proximal end,
   a cartridge holder releasably attached to the distal end of the housing,
   a piston rod engaging a housing insert and a drive member, wherein the piston rod is in threaded engagement with the housing insert,
   a dose setting member guided within the housing to allow rotation of the dose setting member during dose setting and dose dispensing, and
   a clutch for rotationally coupling the drive member and the dose setting member,
   wherein the housing insert is rotationally constrained to the housing and is axially movable together with the drive member relative to the housing between a dose setting position and a dose dispensing position, and wherein during resetting of the drug delivery device, the drive member and an entirety of the housing insert are rotationally de-coupled from the housing.

2. The drug delivery device according to claim 1, further comprising at least one spring biasing the housing insert and the drive member into a resetting position.

3. The drug delivery device according to claim 1, wherein the housing insert and the drive member are coupled such that the housing insert entrains the drive member in an axial movement of the housing insert into the dose setting position and the dose dispensing position and that the drive member entrains the housing insert in an axial movement of the drive member into a resetting position.

4. The drug delivery device according to claim 1, wherein the housing insert and the cartridge holder are coupled such that the cartridge holder entrains the housing insert in an axial movement of the cartridge holder upon attachment of the cartridge holder to the housing.

5. The drug delivery device according to claim 1, wherein the housing insert comprises an inner thread engaging an outer thread of the piston rod.

6. The drug delivery device according to claim 1, further comprising a last dose mechanism with a nut which is in threaded engagement with one of the drive member and the dose setting member and rotationally constrained, but axially movable, relative to the other of the drive member and the dose setting member.

7. The drug delivery device according to claim 1, further comprising a locking element which is rotationally constrained to the housing and is axially movable relative to the housing between a dose setting position, in which the drive member is rotationally constrained to the housing, and a dose dispensing position, in which the drive member is rotationally de-coupled from the housing.

8. The drug delivery device according to claim 7 further comprising at least one spring biasing the housing insert and the drive member into a resetting position and biasing the locking element into the dose setting position.

9. The drug delivery device according to claim 1, wherein the dose setting member is axially constrained to the housing.

10. The drug delivery device according to claim 1, further comprising a drive spring interposed between the housing and the dose setting member.

11. The drug delivery device according to claim 1, further comprising a gauge element radially interposed between the housing and the dose setting member, wherein the gauge element is axially movable relative to the housing and is in threaded engagement with the dose setting member.

12. The drug delivery device according to claim 11, wherein the housing comprises at least one aperture, the gauge element comprises at least one aperture, and an outer surface of the dose setting member comprises markings, wherein at least one of the markings is visible through the aperture of the gauge element and the aperture of the housing during dose setting and dose dispensing.

13. The drug delivery device according to claim 11, wherein the dose setting member comprises a minimum dose rotational counter stop and a maximum dose rotational counter stop.

14. The drug delivery device according to claim 1, wherein the clutch comprises clutch teeth on the drive member and a clutch member rotationally constrained to the dose setting member with corresponding clutch teeth, wherein the clutch member is axially movable together with the drive member relative to the housing into a resetting position in which the clutch member is rotationally de-coupled from the dose setting member.

15. The drug delivery device according to claim 1, comprising a cartridge containing a medicament.

* * * * *